(12) United States Patent
Stepputat et al.

(10) Patent No.: US 7,372,563 B2
(45) Date of Patent: May 13, 2008

(54) METHOD AND DEVICE FOR CARRYING OUT EMISSION SPECTROMETRY

(75) Inventors: Michael Stepputat, Traunstein (DE); Reinhard Noll, Aachen (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 180 days.

(21) Appl. No.: 10/520,123

(22) PCT Filed: Jun. 25, 2003

(86) PCT No.: PCT/EP03/06705

§ 371 (c)(1), (2), (4) Date: Sep. 28, 2005

(87) PCT Pub. No.: WO2004/003528

PCT Pub. Date: Jan. 8, 2004

(65) Prior Publication Data

US 2006/0092415 A1     May 4, 2006

(30) Foreign Application Priority Data

Jul. 1, 2002    (DE)    ................................ 102 29 498

(51) Int. Cl.
*G01J 3/30* (2006.01)
(52) U.S. Cl. ........................ 356/318; 356/316; 356/317
(58) Field of Classification Search ................. 356/318, 356/316, 317
See application file for complete search history.

(56) References Cited

U.S. PATENT DOCUMENTS 5,042,947 A     8/1991    Potzschke et al.
5,702,550 A *   12/1997   Carlhoff et al. ................ 156/64

(Continued)

FOREIGN PATENT DOCUMENTS

DE    40 04 627 A1    2/1991

(Continued)

OTHER PUBLICATIONS

Stepputat M et al., "High-Speed Detection of Additives in Technical Polymers with Laser-Induced Breakdown Spectrometry", Bd. 1667, 2002, Seiten 35-40, XP001155758 Frankfurt, Feb. 26-27, 2002.

*Primary Examiner*—F. L. Evans
*Assistant Examiner*—Abdullahi Nur
(74) *Attorney, Agent, or Firm*—Venable; Robert Kinberg; Henry J. Daley

(57) ABSTRACT

The invention relates to a method and a device for carrying out emission spectroscopy, in particular laser emission spectroscopy. According to said method, a pulsed laser beam is automatically focussed on a workpiece to generate a laser-induced plasma, the radiation emitted from the plasma is detected and an elemental analysis is performed using the captured radiation spectrum. The invention is characterised in that a laser beam impingement is carried out with a variable pulse interval $\Delta T$, that prior to the plasma generation, additional geometric parameters P1, P2 . . . PN of a potential measurement location on the workpiece surface, in addition to the distance d of the autofocus lens from said workpiece surface are determined and in that an elemental analysis is only performed for the potential measurement locations, at which at least one of the additional geometric parameters lies within a predefined tolerance range [T1 . . . T2].

17 Claims, 4 Drawing Sheets

U.S. PATENT DOCUMENTS 5,798,832 A * 8/1998 Hnilica et al. ............... 356/316

FOREIGN PATENT DOCUMENTS

| DE | 41 28 176 A | 2/1993 |
|----|-------------|--------|
| DE | 41 28 176 A1 | 2/1993 |
| DE | 44 26 475 A | 2/1995 |
| DE | 44 26 490 C2 | 10/1996 |

* cited by examiner

METHOD AND DEVICE FOR CARRYING OUT EMISSION SPECTROMETRY

The invention relates to a method and device for quantitative and qualitative multi-elemental analysis of moving test objects using emission spectrometry, in particular laser emission spectrometry.

PRIOR ART

In laser emission spectrometry, the concentration of single chemical elements in a sample is determined by generating a plasma on the surface of the test object with the aid of a focussed laser beam, and the concentration of the observed element in the sample is determined using the element-specific emission of the laser-induced plasma.

FIG. 1 shows the significant values in generating the laser-induced plasma on the surface of a test object. A focussing optic 1 focuses a pulsed laser beam 2 with a propagation direction 3 on a surface element 4 of the test object. The coordination system is selected in such a manner that the propagation direction 3 of the laser beam 2 runs anti-parallel to the z-axis. The normal 5 of the surface element 4 forms an angle α with the z axis, respectively with the axis of the laser beam. The point of penetration 6 of the propagation direction 3 on the surface element 4 is the center of projection 7 of the cross section of the laser beam 2 on the surface element 4. The distance of the focal plane 8 of the laser beam 2 from the point of penetration 6 is referred to as Δs. If the focal plane 8, seen from the focussing optic, lies behind the point of penetration 6 of the focussing optic, this corresponds to positive values for Δs. Typically Δs is selected positive. The distance of the focussing optic 1 from the point of penetration 6 is referred to as d.

The emission of the resulting laser-induced plasma at the site 6 is collected by the receiving optic of the detector unit 9 and conveyed to a spectrometer. The detector unit of the spectrometer determines the time-integrated emission of the observed spectral lines for a defined time window. The concentration of a substance to be analyzed in a sample is determined with the aid of a calibration function for each to-be-analyzed substance from the section-wise time-integrated emission of the observed spectral lines. In this context, it is prior art to calculate the initial value of the calibration function from the ratio of the emission of an observed line of a to-be-analyzed substance to the combination of emissions of other spectral lines, respectively of a measuring signal representative for the overall emission of the plasma.

Laser-emission spectrometry can be operated selectively with a fixed or a variable focal length of the focussing optic.

In laser-emission spectrometry using focussing optics with a fixed focal length, the test object must be positioned precisely down to a few millimeters in order to obtain a quantitative statement about the concentrations of the analyzed elements in the material of the test object by means of a previously carried out calibration. If the position of the sample relative to the fixed focal position of the laser beam or the incline of the surface element 4 is changed, the detected angle of the plasma emission changes due to the changed distance of the sample surface from the fixed position of the receiving optic of the detector unit 9 or due to the test object partially shading the laser-induced plasma. This change can be partly compensated by evaluating the ratio of the measuring signal of the observed emission line to a combination of other line emission signals and to a signal proportional to the overall emission of the observed plasma. This process is called "referencing" or "internal standardization".

Furthermore, another systematic error comes from the changed characteristic of the emission of the laser-induced plasma, making it difficult or impossible to make a quantitative statement about the concentrations of analyzed elements in the material of the test object, respectively there are errors in the measured concentration of the to-be-analyzed substance.

The latter source of errors can be partly remedied by using an auto-focussing unit in conjunction with a pulsed laser with a fixed repetition rate as M. Stepputat et al. VDI-Berichte, 1667, pp. 35-40 (2002) teach. The authors propose using a laser-triangulation sensor in the auto-focussing unit to determine the distance from the sample surface and setting the focal position of the analysis laser to this distance. In this arrangement, the laser beam of the triangulation unit and the laser beam of the analysis laser are disposed coaxially.

DESCRIPTION OF THE INVENTION

Figure 1:
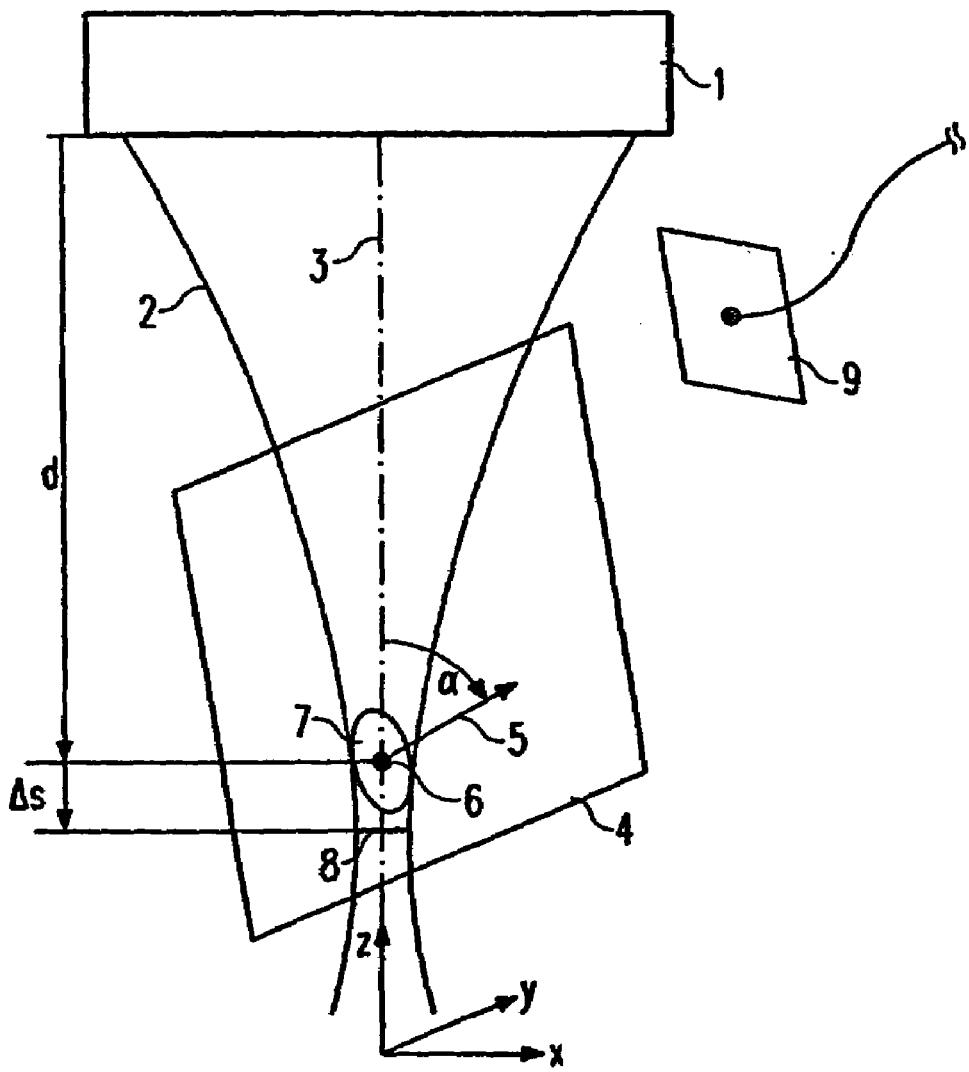
FIG. 1 is a schematic sketch illustrating significant values in generating the laser-induced plasma on the surface of a test object.

The object of the present invention is to provide a method and a device for emission spectrometry, in particular laser-emission spectrometry with improved accuracy, in particular for emission-spectrometry of moving objects.

Solving this object occurs by means of the features of the independent claims. Advantageous further embodiments are given in the dependent claims.

A key element of the present invention is that this object is solved by means of a method in which, prior to plasma generation, additional geometric parameters P1, P2 . . . PN of a potential measurement location on the workpiece are determined in addition to the distance d of the auto-focussing optic from the workpiece surface, an elemental analysis is performed only for the potential measurement locations at which at least one of the additional geometric parameters lies within a predefined tolerance range [T1 . . . T2].

The proposed solution is based on understanding that, according to the prior art, measuring locations whose surfaces are from a geometric standpoint unsuited for quantitative measurement are determined on the test object as well. A prerequisite for as accurate as possible measurement is, namely, that the geometric nature of the measurement location is largely identical with the one present in plotting the calibration curve. If the calibration curve is measured with the geometric parameters P1, P2 . . . PN, the calibration curve only fulfills its intended function of precise calibration if, with otherwise fixed parameters, such as in particular laser parameters, the same geometric parameters are present as in measuring a test object.

To approach this optimum, it is proposed that, in a first step, a tolerance range [T1 . . . T2] is predefined for the geometric parameters P1, P2 . . . PN, which represent as closely as possible the geometric parameters present when performing the calibration. In other words, the predefined geometric parameters should correspond with regard to type and tolerance range to the geometric parameters present in recording the calibration curve. The breadth of the tolerance range of the geometric parameters is yielded by the requirements of the application regarding accuracy in determining the concentration and by the limits set by the employed components.

In a second step, the same geometric parameters P1, P2 . . . PN are measured at potential measurement locations on the workpiece.

In auto-focussing, the distance d of the auto-focussing optic from the workpiece surface is continuously determined as a geometric parameter anyway. In accordance with the present invention, elemental analysis is performed only for the potential measurement locations at which at least one of the additional geometric parameters lies within a predefined tolerance range [T1 . . . T2].

Preferably, one of the geometric parameters is the distance d between the focussing optic and the surface of the workpiece. This distance d, too, should lie accordingly within a tolerance range defined by the calibration measurement. It is pointed out that the tolerance range for the parameter d is independent of the range within which the auto-focussing device still operates reliably.

Furthermore, it is advantageous if the incline a of the surface of the workpiece in relation to the laser beam axis at the potential measurement location is determined as a geometric parameter. By setting this parameter within a tolerance range, it is explicitly taken into account that the emission spectrum of the plasma is dependent on the incline at the measurement location. Systematic reflection of this dependency results, as desired, in increased measuring accuracy.

According to the preceding, the relevant geometric parameters d and α should lie within a tolerance range:

$$d_u \leq d \leq d_o$$

$$-\alpha_{max} \leq \alpha \leq \alpha_{max}$$

These parameters define a process window regarding the geometric parameters within which the emission spectrometry is performed. This manner of proceeding can, of course, be generalized if need be to more relevant geometric parameters.

In order to verify that the measurement locations actually possess geometric parameters within the measurement window, it is provided that prior to plasma inducement, the surface profile of at least one part of the workpiece surface is determined by means of a triangulation process and that the additional geometric parameters are calculated from the surface profile. The current values of the relevant geometric parameters determined in this manner are compared with the predefined desired values, respectively it is checked whether at least one geometric parameter of the measurement location lies within the predefined tolerance range. The accuracy of the measuring result becomes increasingly greater if all the geometric parameters lie within the tolerance range.

Figures 4A, 4B:
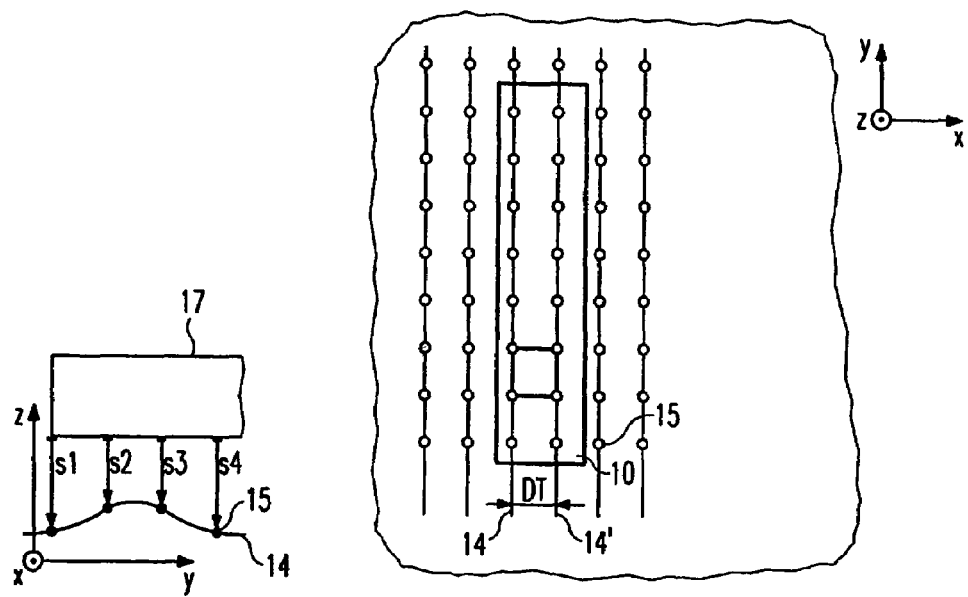
FIG. 4a shows triangulation unit for selecting suited measuring points.
FIG. 4b shows arrangement of surface points of the test object.

In order to permit automatic selection of suited measuring points, means for measuring the surface of the sample are provided which also measure transverse to the direction in which the test object is moving. In this way, for example, in the invented method, the distance d between the surface element 4 and the focussing optic 1 can be determined with the aid of a triangulation unit 17, see FIG. 4a. The arrangement of the surface points 15 of the test object measured is shown schematically in FIG. 4b. A triangulation unit 17 measures simultaneously or in succession the perpendicular distances s1, s2, s3, etc., from a reference plane to the discrete measuring points 15 located on the surface of the test object. The triangulation unit can, for example, be realized by a laser-based section light sensor, a multi-point triangulation unit or multiple triangulation sensors. The distance DT of the lines 14 and 14' to each other is determined by the measuring rate of the triangulation unit and the velocity of the surface of the test object 4'. The course of the sample surface 4' between the measured triangulation measuring points 15 is determined by interpolation.

Consequently, the invented method can be advantageously utilized for examining moving objects. Thus, parts on a belt passing an analysis laser can be measured, for example scrap aluminum parts or scrap electric parts.

Measuring occurs in such a manner that elemental analysis is performed only for the potential measuring locations at which at least one of the additional geometric parameters lies within a predefined tolerance range [T1 . . . T2]. For this, either the data of unsuited measuring locations are rejected or a plasma is induced only at the locations at which the predefined geometric parameters lie within the tolerance range. In the latter case, preferably only a pump pulse and not a laser pulse is released if there is no suited measurement location, thereby increasing the thermal stability of the laser.

Furthermore, it can be provided that the laser beam is deflected transverse to the direction in which the test object is moving. In this manner not only the potential measurement locations are selected in the forward movement direction of the analysis laser but rather also perpendicular to this forward movement direction, thereby increasing the number of evaluatable measuring points on the surface of the test object and thus increasing the accuracy and the reliability of the analysis and identification.

In particular, if the test objects moving quickly relative to the laser beam are small there is the danger that all in all only a few suited measurement points are found. In this case, there is a considerable statistical error in the measuring result. In order to increase measuring accuracy, another aspect of the present invention proposes conducting the method for carrying out the laser-emission spectrometry, in particular for carrying out laser-emission spectrometry, in which a pulsed laser beam is focussed automatically on a workpiece for generating a laser-induced plasma and in which the radiation emitted from the plasma is detected and an elemental analysis is conducted with the detected radiation spectrum, in such a manner that laser beam impingement is carried out with a variable pulse interval $\Delta T$.

The pulse interval can initially be selected in such a manner that the pulse interval is decreased for a high relative velocity between the analysis laser and the test object and increased for a low relative velocity. Similarly, the pulse interval can be selected short for small test objects in order to increase the probability of being able to carry out a measurement. The achieved greater number of possible measurements improves the statistical accuracy of the analysis results.

Preferably, in the pulse variation, a pulse interval is selected whose value lies within a predefined tolerance range [$\Delta T^{min} \ldots \Delta T^{max}$], which increases the system's reliability and stability.

An interval between two laser pulses is designated $\Delta T$ and is usually constant. It can, however, be varied to a limited degree in a laser system. Possible restrictions for the to-be-set pulse interval and therefore for the current repetition rate of the analysis laser can be, for example, increased scattering of the pulse energy, a change in the thermal stability of the analysis laser and due thereto changes in the beam profile or the beam direction, or exceeding the limit values of the pump electronics for generating pump pulses of the laser medium.

The pulse variation is advantageously carried out in such a manner that, in case a suited detection unit, such as for example a light barrier, a triangulation unit or the same, detects a test object, a shorter laser pulse interval is selected for the analysis laser than is the case if no test object is detected. The result of this manner of proceeding is that, if a test object is present, as many as possible measurements are carried out thereby increasing statistical accuracy. However, if the analysis laser detects no test object, the pulse interval is increased thereby allowing the laser to thermalize.

The abovedescribed detecting of additional geometric parameters and measuring only at those locations at which at least one of the additional geometric parameters lies within a predefined tolerance range can now occur alternatively or cumulatively to the pulse variation proposed in the preceding. If both improvements of the method are conducted, this means that, if the analysis laser detects a suited measuring position, a shorter pulse interval is selected than if no suited measuring position is detected. A suited measuring position is a measuring position whose predefined geometric parameters lie within the process window selected by the user. Optimally, therefore is if $\Delta T^{min}$ is selected in the former case and $\Delta T^{max}$ is selected in the latter case.

However, it is to be noted that the laser is under great thermal stress if the laser is shot for a long period with a pulse interval of $\Delta T^{min}$, respectively with a maximum repetition rate. In this case, in order to ensure a stable system, it is necessary to adjust the average pulse interval $\Delta T_{average}$ to the desired value $\Delta T_{desired}$, for which state-of-the-art control methods can be utilized. In other words, the average pulse interval $\Delta T_{average}$ varies around the desired value $\Delta T_{desired}$.

Similarly, it is provided that, if no test object is at the measuring position, the pulse interval is adjusted to the desired value $\Delta T_{desired}$ of the laser system. The desired value $\Delta T_{desired}$ is the pulse interval specified for operation with a fixed repetition rate. However, if a test object is at a measuring position, the pulse interval is selected individually for each pulse. The pulse interval is always set within a system-specific and application-specific range [$\Delta T_{min}$, $\Delta T_{max}$], which also depends on the pulse intervals of the preceding pulses. For each individual pulse interval $\Delta T$, the possible extreme values $\Delta T_{min}$ and $\Delta T_{max}$ are determined anew, respectively the pulse interval $\Delta T$ is set individually for each pulse. The device-based extreme values $\Delta T_g^{min}$ and $\Delta T_g^{max}$ for an individual pulse interval $\Delta T$ and the average pulse interval $\Delta T_{average,N}$ enter via the last N generated laser pulses. The pulse intervals $\Delta T$ of the laser pulses are always selected in such a manner that the average pulse interval $\Delta T_{average,N}$ assumes a value within the range [$\Delta T_{average,N}^{min}$, $\Delta T_{average,N}^{max}$]. This is described in brief by the following terms:

$$\Delta T \in [\Delta T_{min}, \Delta T_{max}]$$

$$\Delta T_{average,N} \in [\Delta T_{average,N}^{min}, \Delta T_{average,N}^{max}]$$

When a test object is located in the measuring position, the values for $\Delta T_{min}$ and $\Delta T_{max}$ are determined according to the following rules:

$$\Delta T_{min} = \Delta T_g^{min} \text{ for } \Delta T_{average,N} > \Delta T_{average,N}^{min}$$

$$\Delta T_{min} = \Delta T_g^{max} \text{ for } \Delta T_{average,N} \leq \Delta T_{average,N}^{min}$$

$$\Delta T_{max} = \Delta T_g^{max} \text{ for } \Delta T_{average,N} < \Delta T_{average,N}^{max}$$

$$\Delta T_{max} = \Delta T_g^{min} \text{ for } \Delta T_{average,N} \geq \Delta T_{average,N}^{max}$$

Figure 2:
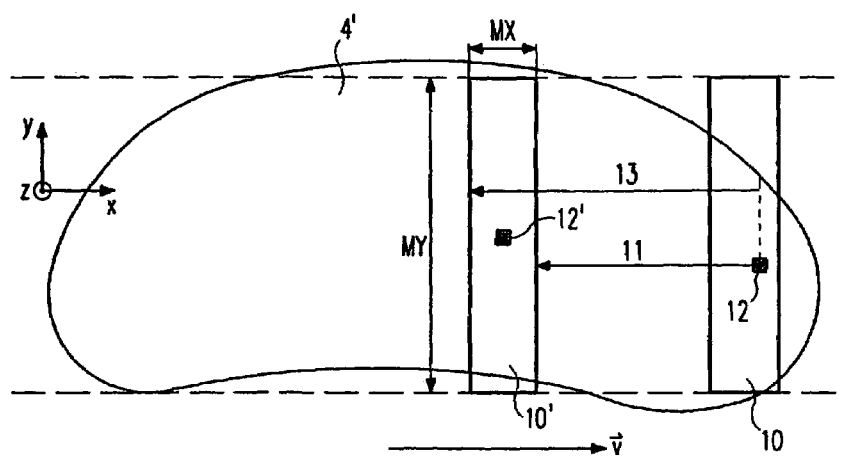
FIG. 2 shows grid of possible measuring regions on the sample surface.

Due to the abovedescribed restrictions of the possible pulse intervals $\Delta T$, if a test object passes the analysis system perpendicular to the beam propagation direction 3 with a constant velocity v, not every desired surface point on the sample surface can be measured. But rather yielded is the grid of possible measuring regions 10 and 10' on the sample surface 4' shown in the FIG. 2. The length MX of a measuring region 10' is yielded by the restrictions of the pulse intervals $\Delta T$. The distance 11 from the last impingement location 12 of the analysis laser 19 in the measuring region 10 to the beginning of the following measuring region 10' yielded by the minimally adjustable pulse interval $\Delta T_{min}$ in conjunction with the velocity v of the test object is $v \times \Delta T_{min}$. Analogously, the end of the measuring region 10' in a distance 13 from the measuring position 12 yielded by the maximally adjustable pulse interval $\Delta T_{max}$ in conjunction with the velocity v of the measuring object is $v \times \Delta T_{max}$.

Figure 3:
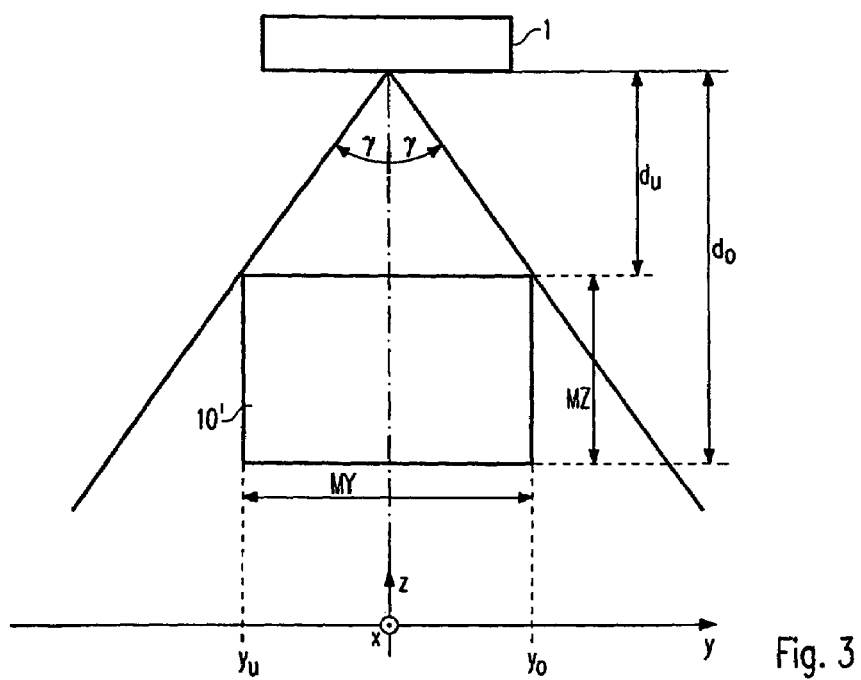
FIG. 3 shows the measuring region in the YZ-plane in rectangular form.

FIG. 3 shows, by way of example, the measuring region 10' in the yz-plane in rectangular form. The height of the measuring region 10' in z-direction is designated MZ and is yielded by the minimally and maximally adjustable distance $d_u$ and $d_o$ of the penetration point 6 to the focussing optic 6. The width MY of the measuring region 10' is determined by the maximally adjustable beam deflection angle γ and the minimally adjustable distance $d_u$ as the boundary of the vertical focussing region MZ. The width MY is selected in such a manner that for each y-coordinate within MY within the maximum beam deflection angle γ, each vertical position z within the focussing region MZ can be reached.

The aim is to localize the next possible measuring position 12' within the measuring window 10' in such a manner that the abovementioned parameters pulse interval $\Delta T$, distance y, distance d and the angle of incline α lie within the process window and the next measurement is conducted solely at this position. The process window is therefore defined as follows:

$$d_u \leq d \leq d_o$$

$$-\alpha_{max} \leq \alpha \leq \alpha_{max}$$

$$y_u \leq y \leq y_o$$

$$\Delta T_{min} \leq \Delta T \leq \Delta T_{max}$$

In order to be able to position the individual laser pulse at the to-be-determined optimum measuring positions 12, 12', the time point when the laser pulse is generated is determined by the system control and the beam of the analysis laser is positioned transverse to the forward movement direction—i.e. in y-direction. By this method, the number of usable measurements on the moving parts are considerably increased in comparison to the prior art.

Figure 5:
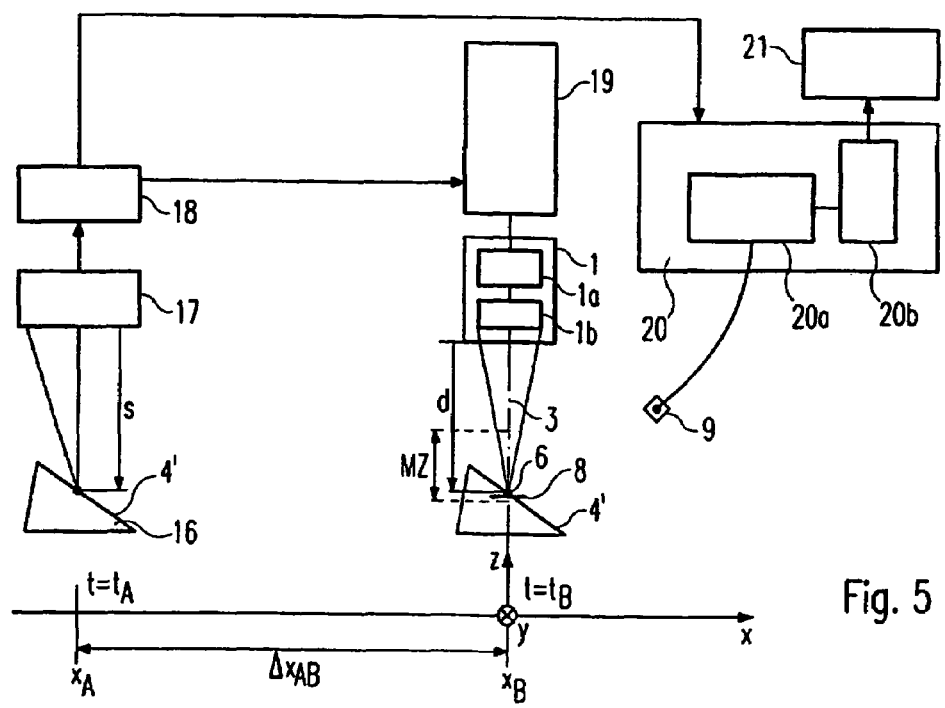
FIG. 5 describes method of carrying out the invention.

FIG. 5 describes carrying out the method. At position $x_A$ at the time point $t_A$, the surface 4' of test object 16 is detected by the triangulation unit 17. For every measured line 14, the distance values s of the triangulation measuring points 15 are transmitted to the autofocus control 18. The autofocus control then determines in the next valid measuring region 10' with the aid of the interpolated course of the surface the next possible measuring point 12', whose parameters ΔT, d and α lie in the valid process window 12'. The search in the next measuring window 10' for a measuring position 12' with a valid process window is preferably sought from short to long ΔT and for each ΔT from short to long distances from the y-coordinate of the measuring position 12 of the preceding measuring region 10. Preferred therefore are measuring points that have within the scope of the possible measuring region 10' a minimal distance from the preceding pulse. In this manner, the maximum possible number of measuring points 12, 12' within the scope of the application are always realized on the sample surface 4'.

If no measuring position 12' can be found in the process window in the measuring region 10', a pump pulse of the laser is released, but no laser pulse is released. The to-be-set pulse interval ΔT is determined as follows:

$$\Delta T = \Delta T_g^{min} \text{ for } \Delta T_{average,N} > \Delta T_{desired}$$

$$\Delta T = \Delta T_g^{max} \text{ for } \Delta T_{average,N} \leq \Delta T_{desired}$$

In this manner, the thermal stability of the laser systems is increased and at the same time the average pulse interval $\Delta T_{average,N}$ is adjusted to the desired value $\Delta T_{desired}$. If only pump pulses but no laser pulses are released for a defined number of pulses and if again only a pump pulse is to be released, a laser pulse whose respective measuring values are rejected is released. This "blind pulse" increases the thermal stability of the laser.

Figure 6:
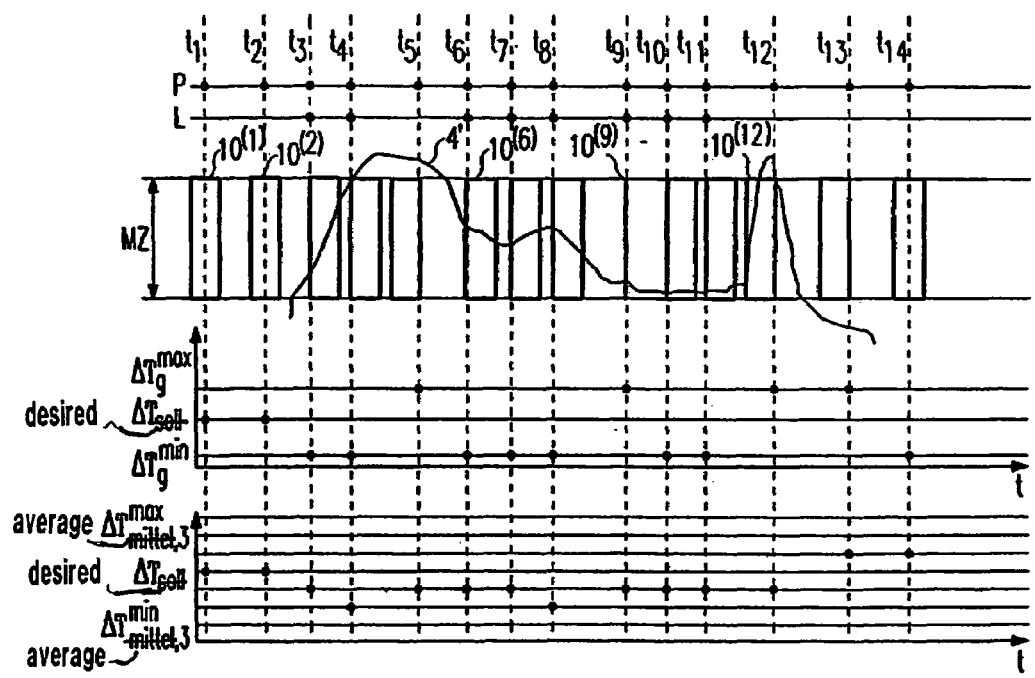
FIG. 6 describes control of the pulse intervals for measuring a test object.

FIG. 6 shows the described control of the pulse intervals for measuring a test object, by way of example, in the xz-plane, the x-axis being indicated by an equivalent time axis (t-axis). P stands for a released pump pulse, L for a released laser pulse. At the time points $t_1$ and $t_2$, there is no measuring object at the measuring position and the pulse intervals are selected $\Delta T_{desired}$. Pump pulses P are released, but no laser pulses L are released. At the time points $t_3$ and $t_4$, the test object is in position, the surface lies in the measuring regions $10^{3'}$, $10^{4'}$ and the two pulse intervals are selected $\Delta T_g^{min}$. This should permit as many successive measurements as possible. Pump pulses P and laser pulses L are released. At the time point $t_5$, no measuring position can be found in the measuring region $10^5$ and therefore the pulse interval of $\Delta T_g^{max}$ is set. A pump pulse P is released, but no laser pulse L is released. At the time point $t_9$, three measurements at the time points $t_6$ to $t_8$ have been conducted with a pulse interval of $\Delta T_g^{min}$ and the average pulse interval over three pulses has already reached the limit value of $\Delta T_{average,3}$. Therefore, $\Delta T_g^{max}$ is yielded as the minimally adjustable pulse interval $\Delta T_{min}$ and the pulse interval ΔT can only be set at $\Delta T_g^{max}$. A suited measuring position is found, and a pump pulse and a laser pulse are released with a pulse interval of $\Delta T_g^{max}$. At the time point $t_{12}$, no position whose parameters lie in the process window can be found in measuring region $10^{12}$. Here the angle α of the surface normals is too large or the surface elements lie outside the vertical measuring region MZ. As the average pulse duration is $\Delta T_{average,3} < \Delta T_{desired}$, the pulse interval is set at $\Delta T_g^{max}$. At the time point $t_{14}$, the test object is no longer at the measuring position and the pulse intervals are once again adjusted to $\Delta T_{desired}$.

For the determined next possible measuring position 12', the parameters ΔT, y and d at the time point $t_B$ of the arrival of the test object 16 at the measuring position $x_B$ are used for focussing the laser beam 2 by the focussing optic 1 at the surface 4' of the test object 16. The focussing optic 1 comprising an auto-focussing optic 1a and the radiation deflection unit 1b focusses the laser beam 2 of the analysis laser 19 on the measuring position $x_B$ on the sample surface 4', see FIG. 5.

To set the position of the laser focus, the procedure is as follows. The vertical distance d is set by the auto-focussing optic 1a. The adjustable vertical measuring region is MZ. The value of the control variable of the auto-focussing optic is selected in such a manner that Δs is constant over all measurements. The y-coordinate of the next measuring position 12' is set by the beam deflection unit 1b. The adjustable region for the horizontal off-setting is MY. The x-coordinate of the next measuring position 12' is set by the time point of the measurement. The length of the adjustable measuring region 10' is MX.

The auto-focussing optic 1a can, for example, be realized with a double lens system comprising a concave and a convex lens. The distance of the focal position to the focussing optic 1 can be varied by moving the concave lens parallel to the optical axis. The deflection unit 1b can, for example, be realized by means of an X/Y-scanner system in conjunction with an F-theta lens.

The emission of the laser-induced plasma 6 generated at the measuring position $x_B$ is collected by the receiving optic of the detector unit 9 and conveyed to the spectrometer 20. The receiving optic of the detector unit 9 is designed in such a manner that plasma emissions can be detected in the entire measuring region MX×MY, see FIG. 2. This can be achieved, for example, by means of a bundle of fibers which is disposed parallel to the y-axis, has a line-shaped cross section at the measuring position, and can detect the plasma emission of each possible measuring location and whose spectrometer-side end is adapted via the change in cross section to the entry gap of the spectrometer and is mounted before it. The dispersion unit 20a of the spectrometer 20 divides the detected plasma emission spectrally and the detector unit 20b of the spectrometer determines for a defined time window the time-integrated emission of the observed spectral lines. The change due to the angle α in the time-integrated plasma emission of all the observed line emissions compared, for example, to the case α=0° is corrected by a correction function f (α). Expressed more generally, if a measured angle of incline α deviates from a predefined value $α_K$, a correction of the emission spectrum is carried out.

The concentration of each observed to-be-analyzed substance in the sample is determined with the aid of a calibration function. For this purpose the detector unit 20b calculates for each laser-induced plasma emission the single reference pulse signals for a line of a to-be-analyzed substance. These are calculated from the ratio of the corrected time-integrated emission of the observed line of to-be-analyzed-substance to a combination of other corrected line emissions, respectively to a combination of a measuring signal that is representative for the entire plasma emission and the vertical distances s1, s2, s3 . . . determined by the triangulation unit 17. All the lines of the to-be-analyzed substances whose time-integrated plasma emission assumes section-wise a value outside the respective measuring region are rejected. Then for each line of the to-be-analyzed-substance, the average value of all the single reference pulse signals belonging to the test object 16 is formed. The concentration of the observed to-be-analyzed substance in the sample is determined via a calibration function into which all the averaged reference single pulse signals of the respective lines of the to-be-analyzed substances are entered. Weighing the averaged single reference pulse signals of the different lines of the to-be-analyzed substances in the calibration function depends on the values of the averaged single reference pulse signals.

The concentrations of the to-be-analyzed substances determined for each test object is transmitted from the detector unit 20b of the spectrometer to a system control 21, which uses these determined concentrations of the to-be-analyzed substances, for example, for sorting test objects, for checking mix-ups or for documentation to ensure quality.

LIST OF DRAWING REFERENCE 1 focussing optic
1a auto-focussing optic
1b beam deflection unit
2 laser beam
3 propagation direction
4 element of the surface of the sample
4' surface of the sample
5 surface normal
6 point of penetration
7 projection of the laser-beam cross section on the surface element
8 focal plane
9 detector unit
10,10' measuring region
11 distance of the last measuring location from the beginning of the following measuring region
12,12' measuring position
13 distance of the last measuring location from the end of the following measuring region
14,14' measuring lines of the triangulation unit
15 point on the sample surface determined by the triangulation unit
16 test object
17 triangulation unit
18 auto-focussing control
19 analysis laser
20 spectrometer
20a dispersion unit of the spectrometer
20b detector unit of the spectrometer
21 system control

What is claimed is:

1. A method for carrying out emission spectrometry, in particular laser emission spectrometry,
    in which a pulsed laser beam is focused automatically on a workpiece to generate a laser-induced plasma,
    in which the radiation emitted by the plasma is detected and elemental analysis is performed with the detected radiation spectrum,
    wherein
    prior to generating the plasma, in addition to determining the distance d of said auto-focusing optic from the surface of said workpiece, additional geometry parameters P1, P2 . . . PN of a potential measuring location on said workpiece surface are determined,
    and an elemental analysis is performed for only the potential measuring locations where at least one of said additional parameters lies within a predefined tolerance range [T1 . . . T2].

2. A method according to claim 1,
    wherein the angle of incline α of said workpiece surface to the axis of said laser beam present at the potential measuring location is determined as a geometric parameter.
3. A method according to claim 2,
    wherein a correction of said emission spectrum is performed if a measured angle of incline α deviates from the predefined value $α_k$.
4. A method according to claim 1,
    wherein prior to plasma inducement, a profile of at least part of said workpiece surface is determined by means of a triangulation process and from said surface profile said additional geometric parameters are calculated.
5. A method according to claim 1,
    wherein a plasma is induced only at those locations at which all said predefined geometric parameters lie within said tolerance range.
6. A method according to claim 1,
    wherein the predefined geometric parameters concerning type and tolerance range correspond to those geometric parameters of which a calibration curve had been plotted.
7. A method according to claim 1,
    wherein said laser beam is deflected transverse to the direction in which said test object is moving.
8. A method according to claim 1,
    wherein parts moving on a belt are measured.
9. A method according to claim 1,
    wherein scrap aluminum or scrap electric parts are measured.
10. A method for carrying out emission spectrometry, in particular for carrying out laser emission spectrometry according to claim 1,
    in which, to generate a laser-induced plasma, a pulsed laser beam is automatically focused on a workpiece,
    in which the radiation emitted by the plasma is detected and elemental analysis is performed using the detected radiation spectrum,
    wherein laser beam impingement occurs with an adjustable pulse interval ΔT.
11. A method according to claim 10,
    wherein the ΔT values lie within a predefined tolerance range $[ΔT_{min} \ldots ΔT_{max}]$.
12. A method according to claim 10,
    wherein if a detection device detects a test object, a shorter pulse interval is selected than if no test object is detected.
13. A method according to claim 10,
    wherein if said detection device detects no test object a pump pulse is released but no laser pulse is released.
14. A method according to claim 10,
    wherein said pulse interval ΔT is set individually for each pulse.
15. A method according to claim 10,
    wherein the limits of said tolerance range $ΔT_{min}$ respectively $ΔT_{max}$ are determined individually for each pulse.
16. A method according to claim 10,
    wherein the pulse interval $ΔT_{average}$ lying in temporal average varies by a desired value $ΔT_{desired}$.
17. A device for emission spectrometry, in particular for laser emission spectrometry, comprising a pulse laser for generating a laser-induced plasma on a workpiece, an auto-focusing device for the laser beam, a detector for detecting the radiation emitted by the plasma and a device for carrying out elemental analysis,
    wherein a unit for deflecting said laser beam provided.

* * * * *